United States Patent
Davis et al.

(10) Patent No.: US 10,272,222 B2
(45) Date of Patent: Apr. 30, 2019

(54) TREATMENT DEVICE AND METHOD OF USE

(75) Inventors: Noel Martin Davis, Stratford Upon Avon (GB); Peter John Bachelor, Stratford Upon Avon (GB)

(73) Assignee: BREAS MEDICAL LIMITED, Stratford-upon-Avon (GB)

( * ) Notice: Subject to any disclaimer, the term of this patent is extended or adjusted under 35 U.S.C. 154(b) by 1123 days.

(21) Appl. No.: 13/876,700

(22) PCT Filed: Sep. 27, 2011

(86) PCT No.: PCT/GB2011/051825
§ 371 (c)(1),
(2), (4) Date: Apr. 22, 2013

(87) PCT Pub. No.: WO2012/042255
PCT Pub. Date: Apr. 5, 2012

(65) Prior Publication Data
US 2013/0220325 A1     Aug. 29, 2013

(30) Foreign Application Priority Data

Sep. 28, 2010 (GB) .................................. 1016304.0
Jun. 13, 2011 (GB) .................................. 1109796.1

(51) Int. Cl.
A61M 16/20 (2006.01)
A61M 16/08 (2006.01)
A61M 16/00 (2006.01)

(52) U.S. Cl.
CPC ........ *A61M 16/20* (2013.01); *A61M 16/0009* (2014.02); *A61M 16/0057* (2013.01);
(Continued)

(58) Field of Classification Search
CPC .. A61M 16/00; A61M 16/04; A61M 16/0402; A61M 16/0427; A61M 16/0434;
(Continued)

(56) References Cited

U.S. PATENT DOCUMENTS 1,338,905 A * 5/1920 Clark .................. A61M 16/104
128/204.28
5,299,568 A * 4/1994 Forare ................. A61M 16/202
128/205.11
(Continued)

FOREIGN PATENT DOCUMENTS

WO 02/32489 A2 4/2002
WO 03/002176 A2 1/2003

OTHER PUBLICATIONS

PCT International Search Report for PCT/GB2011/051825, dated Dec. 13, 2011, applicant: Davis.
(Continued)

*Primary Examiner* — Gregory Anderson
*Assistant Examiner* — Ned T Heffner
(74) *Attorney, Agent, or Firm* — Pedersen and Company, PLLC; Ken J. Pedersen; Barbara S. Pedersen

(57) ABSTRACT

This invention relates to a treatment device (10) and method of use, and in particular to a treatment device adapted to assist the clearance of bronchial secretions in persons whose cough function is impaired. The invention provides a treatment device having a pump (12) with a negative pressure inlet side (22) and a positive pressure outlet side (24). The device has a breathing tube (14) for connection to a patient, and a pressure sensor (18) adapted to determine the pressure within the breathing tube. A valve (16) selectively connects the breathing tube to the inlet side or the outlet side of the pump whereby to provide cycles of positive and negative pressure within the breathing tube. A controller (26) is provided to control the valve. An indicator (20) alerts the
(Continued)

Figure 1:
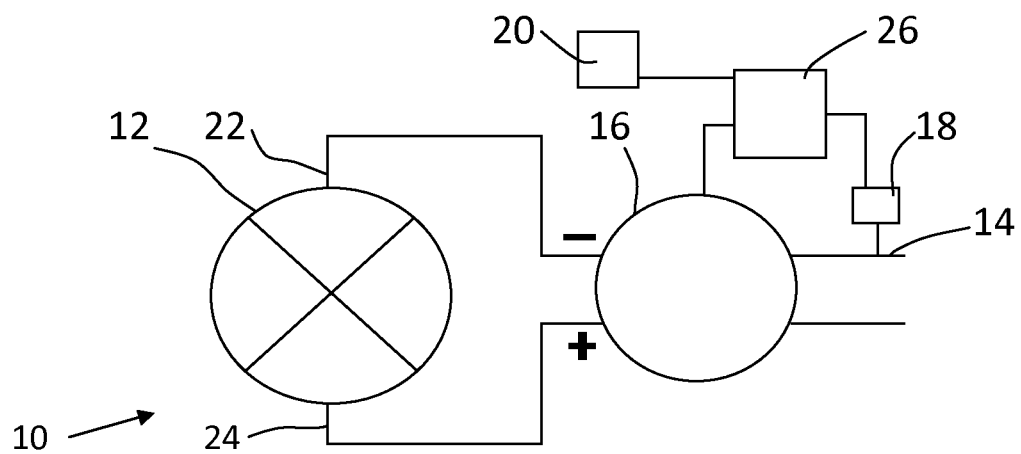

patient to an operational status of the device so that the patient can breathe in time with the device and in particular can seek to cough at the same time as the pressure within the breathing tube is rapidly reduced.

24 Claims, 3 Drawing Sheets

(52) U.S. Cl.
CPC ...... *A61M 16/0069* (2014.02); *A61M 16/022* (2017.08); *A61M 16/0875* (2013.01); *A61M 16/204* (2014.02); *A61M 16/205* (2014.02); A61M 2016/0021 (2013.01); A61M 2205/3337 (2013.01); A61M 2205/581 (2013.01); A61M 2205/583 (2013.01)

(58) Field of Classification Search
CPC ............ A61M 16/044; A61M 16/0445; A61M 16/0454; A61M 16/0456; A61M 16/0459; A61M 16/0465; A61M 16/0488; A61M 16/0497; A61M 16/06; A61M 16/0605; A61M 16/0627; A61M 16/0683–16/0694; A61M 2016/0015–2016/0042; A61M 2016/0413; A61M 2230/00; A61M 2230/005; A61M 2230/202–2230/205; A61M 2230/40–2230/46; A61M 16/22; A61B 5/082–5/097

See application file for complete search history.

(56) References Cited

U.S. PATENT DOCUMENTS

| | | | |
|---|---|---|---|
| 5,345,930 A * | 9/1994 | Cardinal | A61M 16/00 128/204.21 |
| 6,279,574 B1 * | 8/2001 | Richardson | A61M 16/0096 128/204.17 |
| 2005/0039749 A1 * | 2/2005 | Emerson | A61M 16/00 128/204.23 |
| 2007/0193579 A1 | 8/2007 | Duquette et al. | |
| 2007/0199566 A1 * | 8/2007 | Be'eri | A61M 16/0051 128/204.23 |
| 2008/0000477 A1 * | 1/2008 | Huster | A61B 5/091 128/204.23 |

OTHER PUBLICATIONS

PCT International Preliminary Report on Patentability for PCT/GB2011/051825, date of completion: Oct. 16, 2012, applicant: Davis.

\* cited by examiner

TREATMENT DEVICE AND METHOD OF USE

FIELD OF THE INVENTION

This invention relates to a treatment device and method of use, and in particular to a treatment device adapted to assist the clearance of bronchial secretions in persons whose cough function is impaired.

BACKGROUND TO THE INVENTION

Many patients, in particular those suffering from respiratory diseases, are unable to cough for themselves, and require the assistance of a machine which can provide a series of positive and negative pressure cycles, alternately forcing air into the patient's lungs and allowing air to flow out of the patient's lungs. (The term "positive pressure" is used herein to mean a pressure above the ambient atmospheric pressure, and the term "negative pressure" is used to mean a pressure below the ambient atmospheric pressure).

The lungs and bronchial passageways of a person suffering from respiratory disease will usually continue to secrete fluids to keep the bronchial tract moist, as in a healthy person, although in some patients the secretion of fluids may increase as a symptom of the respiratory disease. If the bronchial secretions are allowed to remain in the lungs or bronchial passageways they can impair the lung function and/or harbour germs, and can ultimately cause the death of the patient.

A healthy person is able to cough in order to remove any build-up of bronchial secretions, the cough function forcing air out of the person's lungs at significant force, the moving air also expelling or at least releasing any bronchial secretions which have built up.

A patient suffering from respiratory disease, however, will often not have sufficient cough function, i.e. even if the patient retains the stimulus to cough he or she will not be able to generate sufficient force to cough effectively so as to expel or release any built-up bronchial secretions. Alternative means must therefore be provided to remove the patient's bronchial secretions.

Conventional ventilators which are adapted to assist the breathing of a patient are not able to replicate the cough function.

Physiotherapy is a known treatment to assist the removal of bronchial secretions, the bronchial secretions being released from the lungs of the patient by physical force appropriately applied by a trained person. However, many patients suffering from respiratory disease are treated in the home, and a trained person is not always available to administer the required physiotherapy.

Some ventilators have been modified to provide a "cough programme" which seeks to replicate the cough function in a patient. The cough programme operates by rapidly switching from positive to negative pressure (corresponding to inspiration of the patient and exsufflation of the patient respectively), the output of the pump being varied to control the inspiration and exsufflation pressures. These ventilators suffer from the major drawback that the inspiration pressure and exsufflation pressure cannot be controlled independently. Another major drawback is that the inspiration and exsufflation pressures cannot be altered rapidly, as is often required during ventilation. For example, the patient's face mask may move during the cough programme so that more (or less) of the air being delivered from (or drawn into) the ventilator is passing into (or out from) the patient's lungs.

It is therefore desired to provide a treatment device which can replicate the cough function and which can be used in a person's home without necessarily requiring the assistance of a trained person, and which avoids or reduces the drawbacks of the above-described modified ventilators.

SUMMARY OF THE INVENTION

According to the invention there is provided a treatment device having:
a pump, the pump having an inlet side and an outlet side, the pressure at the inlet side in use being lower than atmospheric pressure, the pressure at the outlet side in use being higher than atmospheric pressure;
a breathing tube for connection to a patient;
a pressure sensor adapted to determine the pressure within the breathing tube;
a valve which can selectively connect the breathing tube to the inlet side or the outlet side of the pump;
a controller adapted to receive a pressure signal from the pressure sensor and to control the valve; and
an indicator to indicate an operational status of the treatment device.

Preferably the valve is a proportional servo valve. The use of a proportional servo valve permits the pressure in the breathing tube to be varied between zero and the maximum pump pressure. Thus, the pressure in the breathing tube is determined by the valve and not by the pump.

Preferably the valve is a proportional solenoid valve, such valves being adapted to rapid movement whereby the pressure in the breathing tube can be set very accurately and can be adjusted quickly if the pressure in the breathing tube changes from the desired level due, for example, to the patient's face mask moving and consequently leaking air. A proportional solenoid valve can permit the pressure in the breathing tube to be adjusted substantially more quickly, and significantly more accurately, than by varying the output of the pump.

Desirably, the proportional servo valve is a rotary proportional solenoid valve. The valve is designed to reciprocate (or oscillate) between operational positions, one operational position corresponding to the breathing tube connected to the inlet side of the pump, the other operational position corresponding to the breathing tube connected to the outlet side of the pump. By switching the valve between these operational positions the pressure within the breathing tube can be altered from positive to negative (and vice versa) very quickly.

In order to replicate a cough function, it is desirable that the pressure profile comprises a gradual increase to a first (positive) pressure, and then a rapid decrease to a second (negative) pressure. This may be followed by a gradual increase to a third (negative) pressure which is maintained for a period of time before the pressure rises to the first pressure once again. The magnitude of the third (negative) pressure is smaller than the magnitude of the second (negative) pressure, i.e. it is closer to atmospheric pressure. The values of the first, second and third pressures, and the durations of each part of the cycle, can be pre-set by the user to match the requirements of a particular patient (although the third (negative) pressure may be pre-set by the device manufacturer).

The second (negative) pressure is therefore ideally a rapid negative spike in pressure lasting for substantially less than one second (e.g. a couple of hundred milliseconds), and the third (negative) pressure is preferably maintained for several seconds. Such a pressure profile facilitates the removal of secretions from the patient's lungs whilst reducing the likelihood of collapsing of the patient's lungs and/or airways (as can occur in some patients if a large-magnitude negative pressure is maintained).

The above pressure profile may be repeated to replicate a second cough, or the device may adopt another profile in which the patient undergoes one (or more) cycle of regular breathing before undertaking another cough cycle.

It is another advantage of a rotary proportional solenoid valve that the operational positions, i.e. the extremes of its reciprocating movement, can be varied. Thus, it can be arranged that the valve move further towards the inlet side of the pump than the outlet side of the pump, or vice versa. Also, it can be arranged that the valve dwells for a longer period of time at its operational position at the inlet side of the pump than at its operational position at the outlet side of the pump. In this way, the value of the negative pressure in the breathing tube will exceed the value of the positive pressure, and the average pressure over a cycle will be lower than atmospheric pressure. The average pressure could alternatively be greater than atmospheric if desired, and the average could change from cycle to cycle. For example, a cough programme could comprise a chosen number of regular breathing cycles (with gradual changes between positive and negative pressures) with an average pressure slightly higher than atmospheric, followed by a cough cycle during which the average pressure is lower than atmospheric pressure.

The indicator is provided for the patient to synchronise his or her breathing with the device, the cough function being better simulated if the patient is trying to breathe out when the device switches from positive pressure to negative pressure.

Desirably, the device has two outlets, one connected to the breathing tube, and another vented to exhaust. Desirably also, when the inlet side of the pump is connected to the breathing tube the outlet side of the pump is connected to exhaust, and vice versa. This minimises or avoids any pressure build-up, or vacuum build-up, within the device.

Preferably, the output of the device is variable, i.e. the treatment device can be adjusted to vary the difference between the positive and negative pressures. Ideally, the pressure range may be varied between substantially zero and 60 cm of water (6,000 Pa). Preferably also the positive pressure can be adjusted independently of the negative pressure, i.e. the positive pressure can be adjusted from approximately 0 to 6,000 Pa and the negative pressure can be independently adjusted from approximately 0 to 6,000 Pa.

Desirably, the period of the cycles of operation, and the individual stages within each cycle, are variable. Preferably, the inspiration period (i.e. positive pressure within the breathing tube) can be adjusted between around 0 and 7 seconds, and the exsufflation period (i.e. negative pressure within the breathing tube) can be adjusted (dependently or independently) between around 0 and 7 seconds. Ideally, both inspiration and exsufflation periods can be adjusted independently from zero to around 5 seconds.

BRIEF DESCRIPTION OF THE PREFERRED EMBODIMENTS

Figure 2:
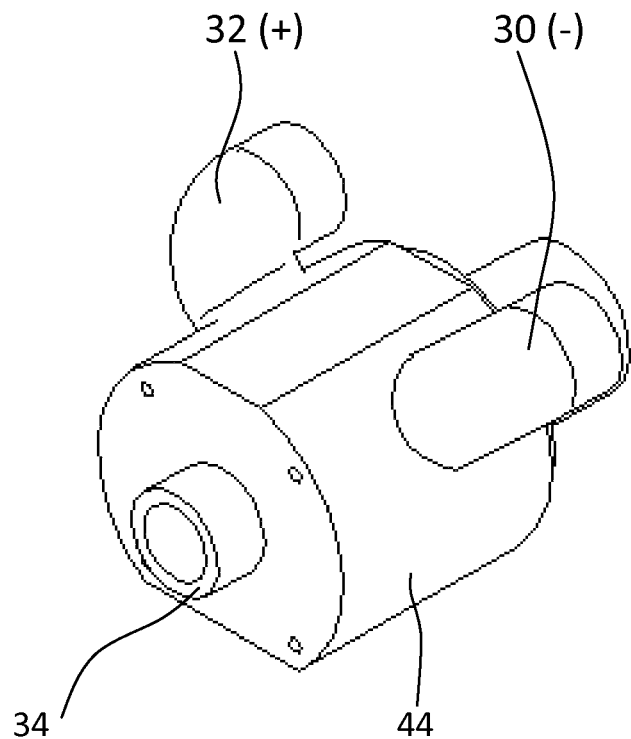
Figure 3:
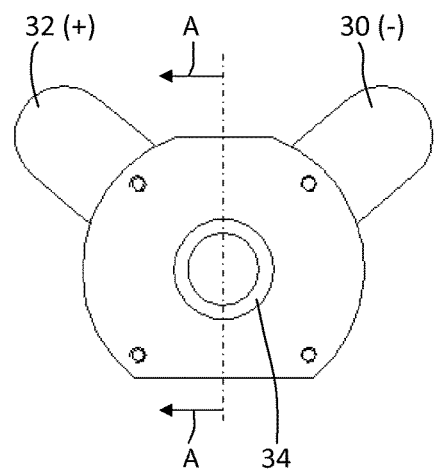
Figure 4:
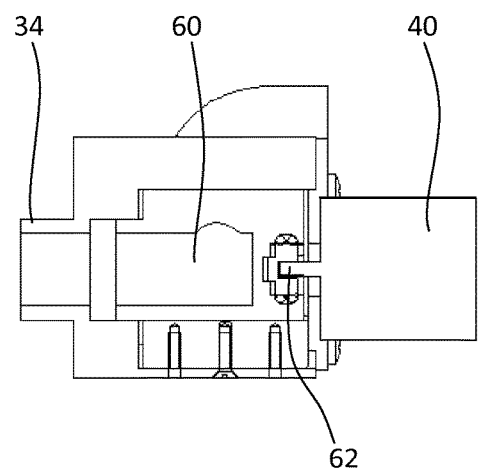
Figure 5:
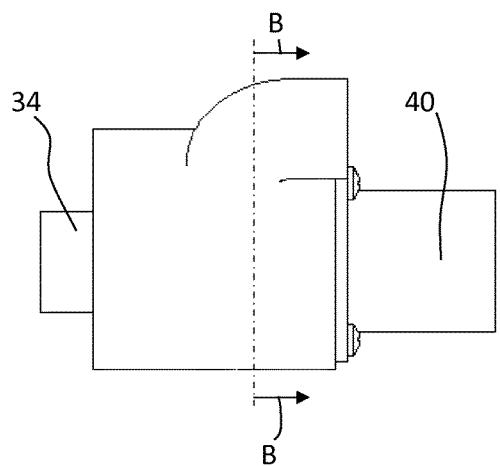
Figure 6:
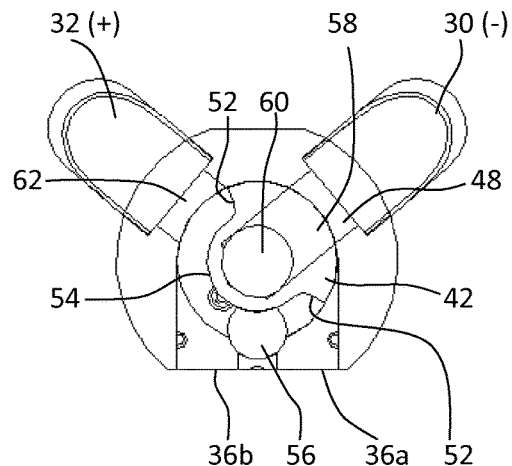
Figure 7:
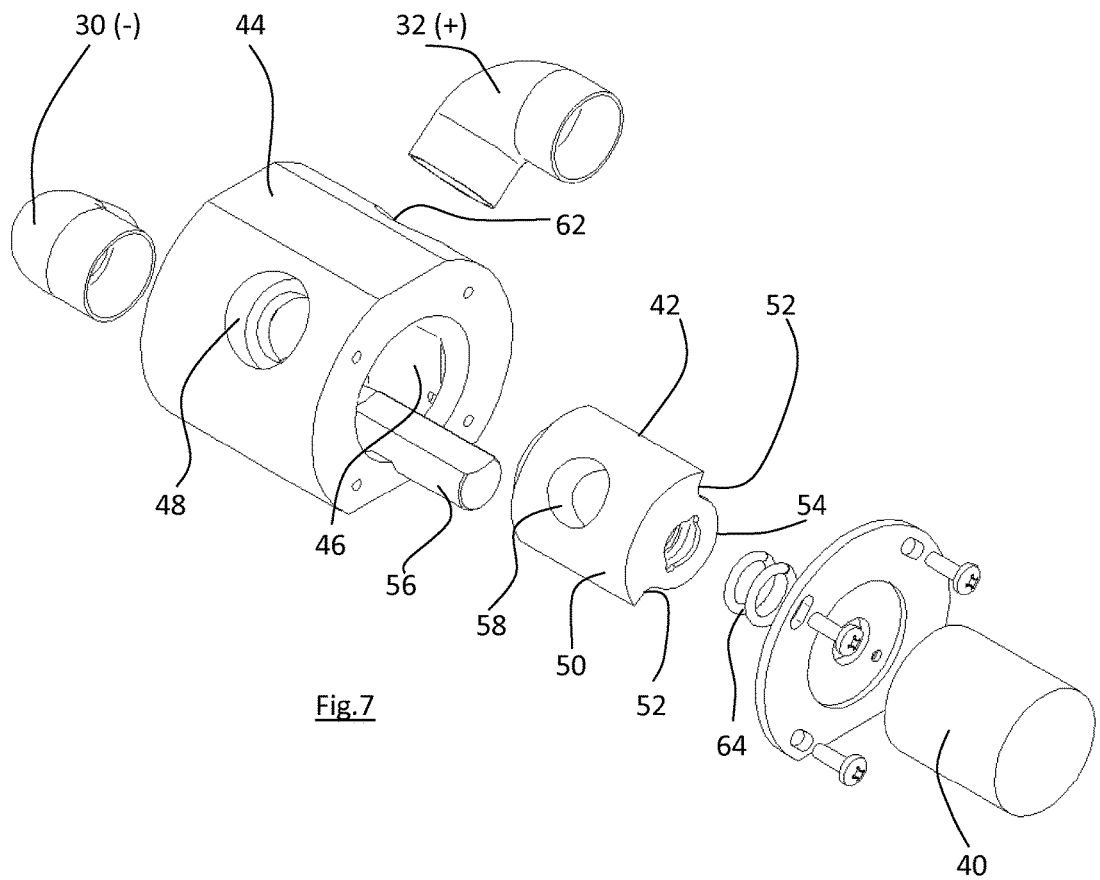
Figure 8:
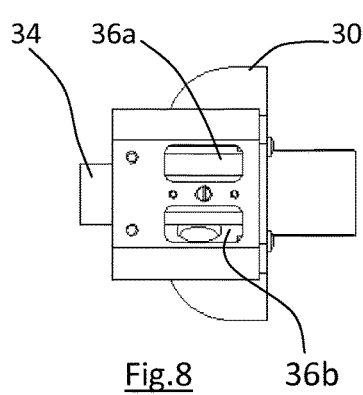
Figure 9:

The invention will now be described in more detail, by way of example, with reference to the accompanying drawings, in which:

FIG. 1 shows a schematic representation of the treatment device of the present invention;

FIG. 2 shows a perspective view of the valve of the device;
FIG. 3 shows an end view of the valve;
FIG. 4 shows a section along the line A-A of FIG. 3;
FIG. 5 shows a side view of the valve;
FIG. 6 shows a section along the line B-B of FIG. 5;
FIG. 7 shows an exploded view of the valve;
FIG. 8 shows an underside view of the valve; and
FIG. 9 shows a detailed view of the valve member.

DETAILED DESCRIPTION

The treatment device 10 comprises a pump 12, a breathing tube 14, a valve 16, a pressure sensor 18 and an indicator 20. The pump has an inlet side 22 and an outlet side 24. The pump preferably includes an impeller (not shown), although other suitable means of generating the required airflow and pressures can be provided. It is a feature of the present invention that the variation in pressure experienced by the patient is provided by the valve 16 rather than the pump 12, and so the pump is not required to provide a rapidly variable pressure and can therefore be of any suitable type.

The pump 12 acts to force air from its inlet side 22 to its outlet side 24, so that in use the pressure at the inlet side 22 is lower than atmospheric pressure and the pressure at the outlet side 24 is higher than atmospheric pressure (represented by the "−" and "+" symbols respectively), in known fashion.

A controller 26 is connected to the valve 16, to the pressure sensor 18 and to the indicator 20. The controller 26 can also be connected to the pump 12 if it is desired to vary the pressures at the inlet 22 and the outlet 24.

The breathing tube 14 is designed to communicate the chosen air flow and pressure to the patient (not shown). In practice, one end of a flexible tube (also not shown), usefully of plastic of the like, will usually be connected to the breathing tube 14, and the other end of the flexible tube will be connected to a face mask adapted to cover the nose and mouth of the patient, the breathing tube, flexible tube and face mask together communicating the air flow to the patient. In some embodiments the flexible tube is integral with the body of the treatment device, but it is preferred that the treatment device have an integral breathing tube to which the flexible tube can be fitted, since this permits replacement of the flexible tube if required.

The pressure sensor 18 is shown in this schematic representation as being connected to the breathing tube 14. Whilst such embodiments would be suitable, it is preferred that the pressure sensor 18 be located within the patient's face mask (not shown), so that a more accurate value for the pressure being experienced by the patient can be obtained. The pressure sensor 18 can be passive, such as the open end of a sensor tube which is connected to the controller 26, the pressure within the face mask being determined at the controller 26. In such embodiments the sensor tube can run alongside or within the flexible tube connecting the face mask to the breathing tube 14. Alternatively the pressure sensor can be active in that it comprises a pressure transducer or the like which can determine the pressure and communicate that (by way of electrical wiring) to the controller.

The valve 16 is shown in more detail in FIGS. 2-9, and in this embodiment is a proportional servo valve (and specifically a rotary proportional solenoid valve). The valve 16 is located between the pump 12 and the breathing tube 14, and has two valve inlets and two valve outlets. The first valve inlet 30 is connected to the inlet side 22 of the pump 12, (and is therefore also represented by the "−" symbol), the second valve inlet 32 is connected to the outlet side 24 of the pump 12 (and is therefore also represented by the "+" symbol). The first valve outlet 34 is connected to the breathing tube 14, and the second valve outlet 36*a,b* (FIG. 8) is connected to exhaust. The second valve outlet 36*a,b* comprises two separate ports 36*a* and 36*b*, which are substantially identical. These ports are separated because one serves to allow the ingress of air from the atmosphere whilst the other allows the egress of air to the atmosphere, as explained in detail below.

The indicator 20 can emit a visual or audible signal (or both). The indicator 20 is connected to the controller 26 and is adapted to alert the patient to the operational status of the treatment device. In particular, the controller 26 issues a signal to the indicator 20 when the treatment device 10 is about to switch from positive to negative pressure during a cough cycle. This permits the patient to breathe out at the same time as the negative pressure is applied, so as to maximise the cough function, and maximise the likelihood of expelling or releasing any built-up bronchial secretions.

The valve 16 is controlled by a rotary proportional solenoid 40 (FIG. 7), the solenoid being connected to the valve member 42 and driving the valve member to oscillate through a chosen angle (in this embodiment up to a maximum of around 55° in each direction) around a central position. The valve body 44 has a central passageway 46 in which the valve member 42 is located, the valve body 44 having ports formed therein, the ports each being connected to a respective valve inlet or valve outlet 30-36.

The valve member 42 has a lobe 50 which is a sliding fit within the central passageway 46, the lobe 50 having two end surfaces 52. The end surfaces 52 define the ends of a reduced-diameter portion 54 of the valve member 42 (see in particular FIG. 6).

FIG. 6 shows the valve member 42 in one of its two extreme positions, with the opening 58 in the lobe 50 of the valve member 42 precisely aligned with (and fully overlapping) the port 48 which is connected to the first valve inlet 30. (It will be understood that in its other extreme position the valve member 42 has been rotated through approximately 110° anticlockwise so that its opening 58 is precisely aligned with the port 62 connected to the valve inlet 32.)

The valve member 42 has a central opening 60 which is connected to the opening 58. The central opening 60 is connected to the breathing tube 14 by way of the first valve outlet 34.

In operation, the proportional solenoid 40 drives the valve member 42 to oscillate clockwise and anticlockwise (as viewed in FIG. 6) between operational positions determined by the controller 26. Whilst FIG. 6 shows the valve member 42 in an extreme position, in which the maximum (negative) pressure at the first valve inlet 30 is communicated to the breathing tube 14 (by way of the central opening 60), the controller 26 can vary the oscillations of the valve member 42 to less extreme positions. For example, in one operational position the valve member could rotate through 40° clockwise from its central position, so that only a proportion of the port 48 is exposed to the opening 58 and the (negative) pressure within the breathing tube 14 is less than the maximum value available from the pump 12. In the other operational position the valve member could rotate through 30° anticlockwise from its central position, so that the positive pressure within the breathing tube 14 is less than the maximum available, and importantly differs in magnitude to (and in particular is less than) the negative pressure during each cycle of oscillation of the valve member.

The proportional solenoid valve 40 is therefore controlled by the controller 26, and the controller 26 reacts to the pressure measured by the sensor 18. The pressure measured by the sensor is compared to the required pressure during that part of the cycle, whereby the operational positions can be determined for (and during) each cycle of operation, and can vary from cycle to cycle as desired, or as required to match a pressure profile set by the user to provide a particular cough programme.

The valve member 42 is adapted to move sufficiently fast to replicate a cough function, i.e. to move rapidly from a position communicating the second valve inlet 32 to the breathing tube 14 to a position communicating the first valve inlet 30 to the breathing tube 14. It is understood that such rapid movement is not necessary during regular breathing cycles, and the proportional solenoid valve 40 can be cycled more slowly during regular breathing cycles. Preferably, however, even during regular breathing cycles the valve member 42 is moved rapidly between operational positions, and the operational position (or positions) is (are) adjusted so as to match the desired pressure profile. The operational position can be adjusted during the cycle so as to maintain the pressure within the breathing tube 14 as desired during that part of the cycle, i.e. the overlap between the opening 58 and the port 48 (and between the opening 58 and the port 62, as appropriate) can be adjusted during a breathing cycle to maintain the pressure profile which has been pre-set by the user. The rapid operation of the valve can be advantageous even during regular breathing cycles in that the operational position can be adjusted to quickly provide a greater or lower pressure in the event that the pressure within the breathing tube decreases or increases, perhaps because the face mask moves relative to the patient.

In the position shown in FIG. 6, the breathing tube 14 to the patient experiences a negative pressure. The value of the negative pressure is determined by the operational position of the valve member 42 and can be any pressure between zero and the maximum negative pressure available from the pump 12. In practice, the output of the pump 12 will be chosen to provide a maximum negative pressure within the breathing tube of around 6,000 Pa, but the maximum can be another value chosen to suit a particular patient or group of patients.

The negative pressure part of the cycle is maintained for a chosen period of time (i.e. the valve member 42 remains substantially in the position shown in FIG. 6), again ideally dependent upon the particular patient or group of patients for which the treatment device 10 is designed. In a desired embodiment the negative pressure part of the cycle can be maintained from substantially zero seconds to around 7 seconds.

Whilst the first valve inlet 30 is connected to the central opening 60 as shown in FIG. 6, the exhaust port 36*b* is connected, by way of the reduced diameter portion 54 of the valve member 42, to the second valve inlet 32, whereby air can flow from the atmosphere to the inlet side 22 of the pump 12.

At the end of the negative pressure part of the cycle the solenoid 40 is actuated to drive the valve member 42 (anticlockwise as viewed in FIG. 6) to another operational position in which the opening 58 in the valve member 42 is at least partially aligned with the port 62 of the second valve inlet 32. The second valve inlet 32 is connected to the outlet or positive pressure side 24 of the pump 12. Accordingly, the pressure within the central opening 60, and therefore the pressure within the breathing tube 14, rises to a value determined by the angular position of the valve member 42.

Preferably, the valve member 42 moves rapidly to its extreme anticlockwise position so that the maximum airflow occurs from the pump 12 to the breathing tube 14 and the pressure within the breathing tube rises towards its chosen value. As the pressure within the breathing tube approaches the value which has been set by the user, the valve member 42 can move towards its central position, reducing the airflow into the breathing tube 14. When the desired positive pressure within the breathing tube is attained the valve member 14 can close further so that the airflow matches the leaks within the system and the desired pressure can be maintained for the chosen period.

Whilst the treatment device 10 can be arranged to undertake a series of positive and negative pressure cycles, and therefore replicate a conventional ventilator, it is designed primarily to replicate a patient's cough function. Accordingly, after a chosen number of regular breathing cycles which enable the patient to synchronise his or her breathing with the device, the device undergoes a cough cycle in which the pressure within the breathing tube moves rapidly from a chosen positive pressure to a chosen negative pressure. Ideally, the positive pressure and the negative pressure are chosen by the user and are pre-set into the controller 26.

During a cough cycle the proportional solenoid 40 moves the valve member 42 from a first operational position (providing a positive pressure) to a second operational position (providing a negative pressure) in a fraction of a second, so that the pressure change within the breathing tube 14 is substantially instantaneous. Such a pressure change within the lungs of a patient can simulate the coughing action, and can expel or release bronchial secretions which have built up in the patient's lungs or bronchial passageways.

The negative pressure is held for a predetermined time. The predetermined time may be several seconds, but for some patients the maintenance of a large negative pressure (as required for an effective cough function) can be counterproductive because the patient's lungs and/or airways can collapse under the negative pressure. For such patients the device should not maintain the negative pressure but instead should provide a rapid negative pressure spike lasting for substantially less than one second (e.g. a couple of hundred milliseconds) and then reduce the magnitude of the negative pressure towards atmospheric pressure. The reduced magnitude negative pressure can be maintained for several seconds to facilitate the removal of secretions whilst reducing the likelihood of collapse of the patient's lung/airways. The reduced magnitude negative pressure can be pre-set by the user if desired, but will usually be pre-set by the manufacturer of the treatment device.

During the cough cycle, the indicator 20 will indicate to the patient, either visually, audibly or both, that the treatment device is about to switch from positive pressure to negative pressure, so that the patient can (perhaps with practice) synchronise his or her breathing with the reduction in pressure so as to maximise the cough function.

It will be understood from FIG. 6 that during the positive pressure part of a cycle in which the second valve inlet 32 is connected to the central opening 60, the first valve inlet 30 is connected to the exhaust port 36a. Air can enter through the port 36a and pass through the first valve inlet 30 to the inlet side 22 of the pump 12.

The period during which the patient experiences positive pressure can ideally be varied from between substantially zero and around 7 seconds. Also, the positive pressure experienced can preferably be varied from around zero to the maximum available from the pump 12, i.e. around 6,000 Pa by varying the operational position of the valve member 42. Typically, however, the positive pressure during a cycle would be of lower magnitude than the negative pressure, i.e. a patient undergoing a cough programme would for example experience a positive pressure of around 3,000 Pa and a negative pressure of around 6,000 Pa.

In the embodiment shown the dam or blocking member 56 (which acts to separate the port 36a from the port 36b, is a separate component mounted upon the valve body 44, but it will be understood that this part could instead be made integral with the valve body.

Ideally, the valve body 44 and valve member 42 are made of plastics materials. The use of such materials reduces the need for additional bearings to centralise the moving components. Ideally the lobe 50 of the valve member 42 is a sliding fit within the central passageway 46.

The invention claimed is:

1. A treatment device (10) having:
a pump (12), the pump having an inlet side (22) and an outlet side (24), the pressure at the inlet side in use being lower than atmospheric pressure, the pressure at the outlet side in use being higher than atmospheric pressure;
a breathing tube (14) for connection to a patient;
a pressure sensor (18) adapted to measure the pressure within the breathing tube;
a valve (16) located between the pump (12) and the breathing tube (14), the valve being adapted to selectively connect the breathing tube to the inlet side (22) or the outlet side (24) of the pump, the valve having a first valve inlet (30) connected to the inlet side (22) of the pump (12) and a second valve inlet (32) connected to the outlet side (24) of the pump (12), the first valve inlet (30) having a first valve inlet port (48) and the second valve inlet (32) having a second valve inlet port (62), the valve (16) having a valve member (42) with a valve opening (58), the valve opening (58) being connected to the breathing tube (14), the valve member being movable between a first operational position in which the valve opening (58) overlaps the first valve inlet port (48) and a second operational position in which the valve opening (58) overlaps the second valve inlet port (62);
a controller (26) adapted to receive a pressure signal from the pressure sensor (18) and to control the movement of the valve member (42), the controller (26) being adapted to determine the first operational position according to the amount of overlap required between the valve opening (58) and the first valve inlet port (48) in order to provide a predetermined negative pressure within the breathing tube, and to determine the second operational position according to the amount of overlap required between the valve opening (58) and the second valve inlet port (62) in order to provide a predetermined positive pressure within the breathing tube, the controller (26) determining the first operational position independently of the second operational position;
the amounts of overlap between the valve opening and the respective first valve inlet port and the second valve inlet port each being independently variable to comprise multiple proportions of overlap greater than no overlap and less than full overlap, so that the predetermined negative pressure is variable to comprise multiple negative pressures between atmospheric pressure and a maximum negative pressure available from the pump, so that the predetermined positive pressure is variable to comprise multiple positive pressures between atmospheric pressure and a maximum positive pressure available from the pump, and so that the predetermined negative pressure is independent of the predetermined positive pressure; and an indicator (20) operatively connected to the controller (26), the indicator (20) being configured to indicate an operational status of the treatment device whereby the patient can synchronize his or her breathing with the device during use.

2. The treatment device (10) according to claim 1 in which the valve member (42) is able to reciprocate between its first and second operational positions.

3. The treatment device (10) according to claim 1 in which the controller (26) can adjust the first and second operational positions of the valve member (42) during use.

4. The treatment device (10) according to claim 1 in which the first and second operational positions can be varied whereby the magnitudes of the negative and positive pressures within the breathing tube (14) can be varied between substantially zero and approximately 6,000 Pa.

5. The treatment device (10) according to claim 1 in which the pressure sensor (18) is a pressure transducer.

6. The treatment device (10) of claim 1 having a valve body (44) with two outlets (60), one outlet (60) being connected to the breathing tube, the other outlet (36*a,b*) being open to the atmosphere.

7. The treatment device (10) of claim 1 in which, when the inlet side (22) of the pump (12) is connected to the breathing tube (14) the outlet side (24) of the pump is connected to atmosphere, and vice versa.

8. The treatment device (10) of claim 1 in which, in the first operational position the valve opening (58) does not overlap the second valve inlet port (62), and in the second operational position the valve opening (58) does not overlap the first valve inlet port (48).

9. The treatment device (10) according to claim 1 in which the valve is a proportional servo valve (16).

10. The treatment device (10) according to claim 9 in which the proportional servo valve is a rotary proportional solenoid valve (16).

11. The treatment device (10) according to claim 1 in which the controller (26) can vary the duration for which the valve member (42) remains in each of its operational positions.

12. The treatment device (10) according to claim 11 in which the controller (26) can vary the duration for which the valve member (42) remains in each of its operational positions during use.

13. The treatment device (10) according to claim 11 in which the duration for which the valve member (42) remains in each of its operational positions can be varied from approximately 0 seconds to approximately 7 seconds.

14. The treatment device (10) according to claim 11 in which the duration for which the valve member (42) remains in its first operational position and in its second operational position can be varied, independently, from zero to approximately 5 seconds.

15. A method of treating a patient comprising the following steps:
providing a treatment device according to claim 1;
connecting the breathing tube to a patient;
undertaking a pressure cycle, the pressure cycle including a rapid decrease in pressure in the breathing tube whereby to replicate the patient's cough function, the rapid decrease in pressure within the breathing tube being provided by movement of the valve.

16. The method according to claim 15 in which the treatment device provides a positive pressure of pre-set magnitude and a negative pressure of pre-set magnitude, the magnitude of the negative pressure exceeding the magnitude of the positive pressure.

17. The method of treatment according to claim 15 in which the pressure cycle comprises an increase to a pre-set positive pressure, and then a rapid decrease to a pre-set negative pressure, followed by an increase to a pre-set negative pressure of smaller magnitude.

18. The method of treatment according to claim 17 in which the increase to the pre-set positive pressure is gradual.

19. The method according to claim 17 in which the positive pressure and the larger-magnitude negative pressure are pre-set by the user.

20. The method according to claim 17 in which the smaller-magnitude negative pressure is pre-set by the treatment device manufacturer.

21. The method of treatment according to claim 17 in which the pressure is substantially maintained at the larger-magnitude pre-set negative pressure for substantially less than one second.

22. The method of treatment according to claim 21 in which the pressure is substantially maintained at the larger-magnitude pre-set negative pressure for approximately two hundred milliseconds.

23. The method according to claim 15 in which the average pressure within the breathing tube over an operational cycle is lower than atmospheric pressure.

24. The method according to claim 23 in which the average pressure changes from one cycle to the next cycle.

* * * * *